United States Patent
Mirarchi et al.

[11] Patent Number: 5,865,800
[45] Date of Patent: Feb. 2, 1999

[54] DEFLECTABLE CATHETER

[75] Inventors: Thomas F. Mirarchi, Shrewsbury; Josef V. Koblish, Wellesley; Kulbir S. Hunjan, Natick, all of Mass.; Craig R. Kline, Spencer, Ind.; Thomas H. Peterson, Plainville, Mass.

[73] Assignee: Boston Scientific Corporation, Natick, Mass.

[21] Appl. No.: 727,077

[22] Filed: Oct. 8, 1996

Related U.S. Application Data

[63] Continuation of Ser. No. 138,863, Oct. 19, 1993, Pat. No. 5,562,619, which is a continuation-in-part of Ser. No. 109,609, Aug. 19, 1993, Pat. No. 5,376,094.

[51] Int. Cl.⁶ .......................... A61M 37/00; A61B 17/36
[52] U.S. Cl. .................................. 604/95; 606/41
[58] Field of Search ............................ 604/95, 280, 264, 604/281, 282, 164; 606/1, 32, 34, 41, 108; 600/433–435, 585

[56] References Cited

U.S. PATENT DOCUMENTS

| | | |
|---|---|---|
| Re. 34,502 | 1/1994 | Webster, Jr. . |
| 2,118,631 | 5/1938 | Wappler . |
| 2,688,329 | 9/1954 | Wallace . |
| 3,416,531 | 12/1968 | Edwards . |
| 3,452,740 | 7/1969 | Muller . |
| 3,452,742 | 7/1969 | Muller . |
| 3,470,876 | 10/1969 | Barchilon . |
| 3,485,234 | 12/1969 | Stevens . |
| 3,500,820 | 3/1970 | Almen . |
| 3,503,385 | 3/1970 | Stevens . |
| 3,521,620 | 7/1970 | Cook . |
| 3,547,103 | 12/1970 | Cook . |
| 3,552,384 | 1/1971 | Pierie et al. . |
| 3,605,725 | 9/1971 | Bentov . |
| 3,625,200 | 12/1971 | Muller . |
| 3,631,848 | 1/1972 | Muller . |
| 3,749,086 | 7/1973 | Kline et al. . |
| 3,773,034 | 11/1973 | Burns et al. . |
| 3,847,140 | 11/1974 | Agella ..................................... 128/772 |

(List continued on next page.)

FOREIGN PATENT DOCUMENTS

| | | |
|---|---|---|
| 0 183 585 A2 | 6/1986 | European Pat. Off. . |
| 0 301 288 A1 | 2/1989 | European Pat. Off. . |
| 0 397 489 A1 | 11/1990 | European Pat. Off. . |
| 0 521 595 A2 | 1/1993 | European Pat. Off. . |
| 2 501 995 | 9/1992 | France . |
| 2 130 885 | 6/1984 | United Kingdom . |
| WO 91/11213 | 8/1991 | WIPO . |
| WO 93/08757 | 5/1993 | WIPO . |
| WO 93/08869 | 5/1993 | WIPO . |
| WO 93/16628 | 9/1993 | WIPO . |
| WO 93/24050 | 12/1993 | WIPO . |

OTHER PUBLICATIONS

Jackman, Warren M., M.D., et al.; "New Catheter Technique for Recording Left Free–Wall Accessory Atrioventricular Pathway Activation", Part 1, vol. 78, No. 3, (Sep. 1988).

*Primary Examiner*—Glenn K. Dawson
*Attorney, Agent, or Firm*—Henricks, Slavin & Holmes LLP

[57] ABSTRACT

For achieving, e.g., an improved electrophysiology catheter for examination of the heart, or a catheter accessing the brain, the invention, in one aspect, features an elongated wound wire coil extending through the hollow catheter body of a steerable catheter. The coil is constructed and arranged to enable the catheter body to withstand reactive compressive load without distortion during application of tension on the pull wire and to transmit torque from the proximal to the distal tip portion of the catheter to enhance fidelity of rotational positioning of the distal tip in response to rotational orientation of the proximal portion of the catheter. The coil is shown in frictional torque-transmitting relationship with the interior of the hollow shaft substantially along the common length of the catheter body when the catheter is bent. Steerable catheters with augmented throw for one-handed operation and important improvements in construction features are also shown.

25 Claims, 7 Drawing Sheets

U.S. PATENT DOCUMENTS

| | | |
|---|---|---|
| 3,854,473 | 12/1974 | Matsuo . |
| 3,906,938 | 9/1975 | Fleischhacker . |
| 3,924,632 | 12/1975 | Cook . |
| 3,973,556 | 8/1976 | Fleischhacker et al. . |
| 4,003,369 | 1/1977 | Heilman et al. . |
| 4,020,829 | 5/1977 | Willson et al. . |
| 4,033,331 | 7/1977 | Guss et al. . |
| 4,080,706 | 3/1978 | Heilman et al. . |
| 4,215,703 | 8/1980 | Willson . |
| 4,239,042 | 12/1980 | Asai . |
| 4,245,624 | 1/1981 | Komiya . |
| 4,351,341 | 9/1982 | Goldberg et al. . |
| 4,365,639 | 12/1982 | Goldreyer . |
| 4,409,993 | 10/1983 | Furihata . |
| 4,444,188 | 4/1984 | Bazell et al. . |
| 4,444,195 | 4/1984 | Gold . |
| 4,456,017 | 6/1984 | Miles ................................. 128/772 |
| 4,468,224 | 8/1984 | Enzmann et al. . |
| 4,516,972 | 5/1985 | Samson ............................... 604/282 |
| 4,561,439 | 12/1985 | Bishop et al. . |
| 4,577,629 | 3/1986 | Martinez . |
| 4,586,923 | 5/1986 | Gould et al. ......................... 604/95 |
| 4,597,755 | 7/1986 | Samson et al. . |
| 4,614,188 | 9/1986 | Bazell et al. . |
| 4,633,880 | 1/1987 | Osypka et al. . |
| 4,650,467 | 3/1987 | Bonello et al. . |
| 4,660,571 | 4/1987 | Hess et al. . |
| 4,664,113 | 5/1987 | Frisbie et al. . |
| 4,677,990 | 7/1987 | Neubauer . |
| 4,682,596 | 7/1987 | Bales et al. . |
| 4,719,924 | 1/1988 | Crittenden et al. . |
| 4,723,936 | 2/1988 | Buchbinder et al. .................. 604/95 |
| 4,748,986 | 6/1988 | Morrison et al. . |
| 4,757,827 | 7/1988 | Buchbinder et al. . |
| 4,777,955 | 10/1988 | Brayton et al. . |
| 4,787,399 | 11/1988 | Bonello et al. . |
| 4,798,193 | 1/1989 | Giesy et al. . |
| 4,798,598 | 1/1989 | Bonello et al. ....................... 604/280 |
| 4,830,023 | 5/1989 | de Toledo et al. . |
| 4,832,048 | 5/1989 | Cohen . |
| 4,886,067 | 12/1989 | Palermo . |
| 4,911,148 | 3/1990 | Sosnowski et al. . |
| 4,920,980 | 5/1990 | Jackowski ............................ 604/95 |
| 4,922,912 | 5/1990 | Watanabe . |
| 4,940,062 | 7/1990 | Hampton et al. . |
| 4,955,382 | 9/1990 | Franz et al. . |
| 4,957,110 | 9/1990 | Vogel et al. . |
| 4,960,134 | 10/1990 | Webster, Jr. ......................... 128/786 |
| 4,960,411 | 10/1990 | Buchbinder .......................... 604/95 |
| 4,979,510 | 12/1990 | Franz et al. . |
| 4,998,916 | 3/1991 | Hammerslag et al. ................ 604/95 |
| 5,005,587 | 4/1991 | Scott . |
| 5,052,404 | 10/1991 | Hodgson . |
| 5,060,660 | 10/1991 | Gambale et al. . |
| 5,069,674 | 12/1991 | Fearnot et al. . |
| 5,084,012 | 1/1992 | Kelman . |
| 5,117,828 | 6/1992 | Metzger et al. . |
| 5,125,895 | 6/1992 | Buchbinder et al. . |
| 5,125,896 | 6/1992 | Hojeibane . |
| 5,131,406 | 7/1992 | Kaltenbach . |
| 5,154,705 | 10/1992 | Fleischhacker et al. . |
| 5,165,421 | 11/1992 | Fleischhacker et al. . |
| 5,170,803 | 12/1992 | Hewson et al. . |
| 5,172,699 | 12/1992 | Svenson et al. . |
| 5,178,158 | 1/1993 | de Toledo . |
| 5,190,050 | 3/1993 | Nitzsche ............................... 128/772 |
| 5,195,968 | 3/1993 | Lundquist et al. .................... 604/95 |
| 5,195,991 | 3/1993 | Pike . |
| 5,209,727 | 5/1993 | Radisch, Jr. et al. . |
| 5,215,103 | 6/1993 | Desai . |
| 5,217,465 | 6/1993 | Steppe . |
| 5,222,501 | 6/1993 | Ideker et al. . |
| 5,222,938 | 6/1993 | Behl . |
| 5,226,430 | 7/1993 | Spears et al. . |
| 5,228,441 | 7/1993 | Lundquist ............................. 604/95 |
| 5,230,349 | 7/1993 | Langberg . |
| 5,231,995 | 8/1993 | Desai . |
| 5,239,999 | 8/1993 | Imran . |
| 5,254,088 | 10/1993 | Lundquist et al. .................... 604/95 |
| 5,254,112 | 10/1993 | Sinofsky et al. . |
| 5,255,678 | 10/1993 | Deslauriers et al. . |
| 5,255,679 | 10/1993 | Imran . |
| 5,263,493 | 11/1993 | Avitall . |
| 5,269,319 | 12/1993 | Schulte . |
| 5,273,535 | 12/1993 | Edwards et al. . |
| 5,275,162 | 1/1994 | Edwards et al. . |
| 5,281,218 | 1/1994 | Imran . |
| 5,285,004 | 2/1994 | Lashinski . |
| 5,293,868 | 3/1994 | Nardella . |
| 5,327,906 | 7/1994 | Fideler ................................. 604/95 |
| 5,330,466 | 7/1994 | Imran ................................... 604/95 |
| 5,334,145 | 8/1994 | Lundquist et al. .................... 604/95 |
| 5,562,619 | 10/1996 | Mirarchi et al. ...................... 604/95 |

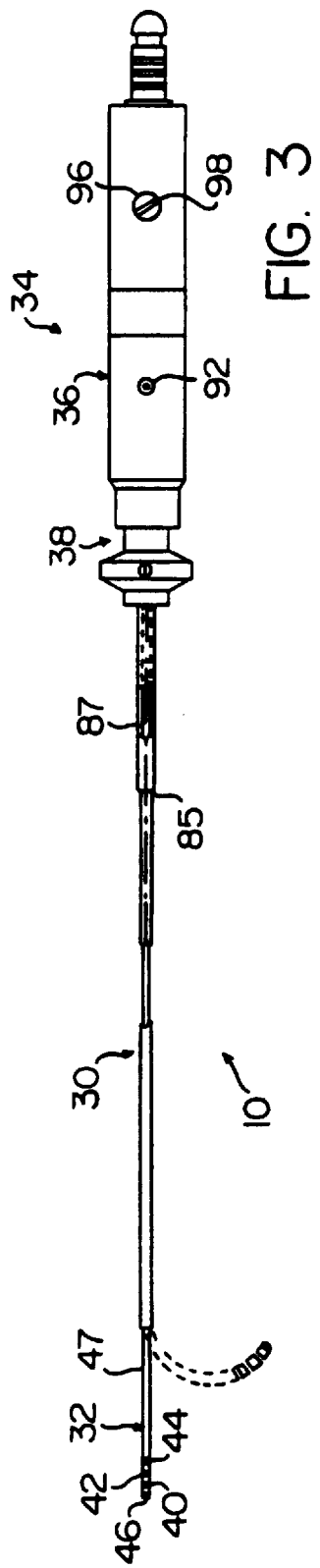
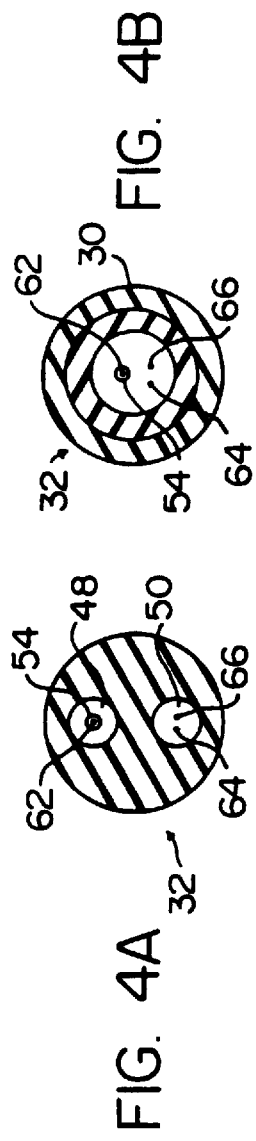
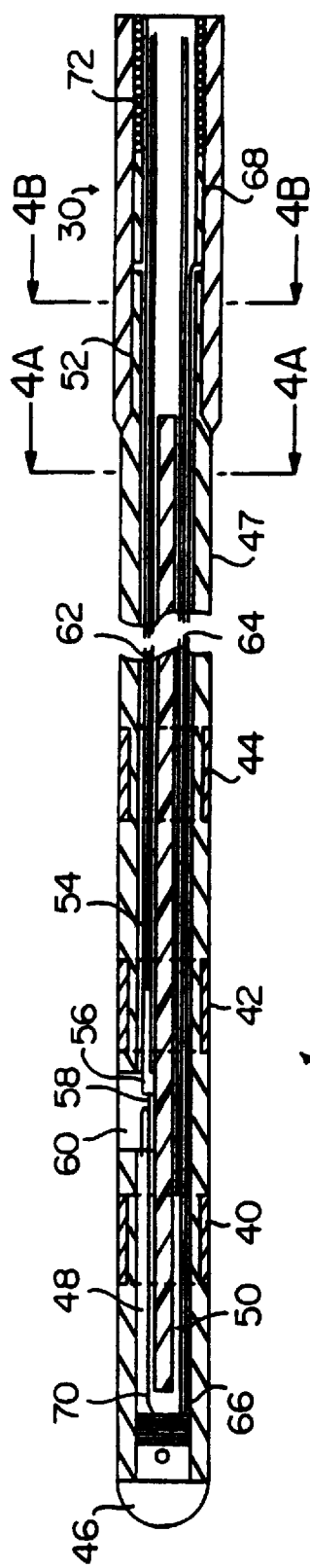

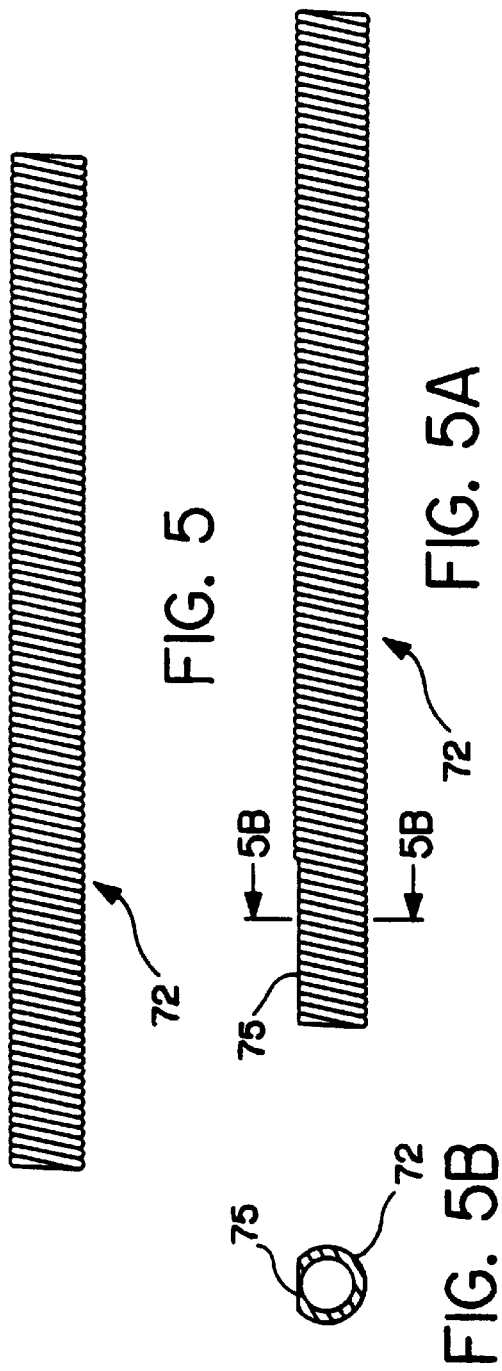
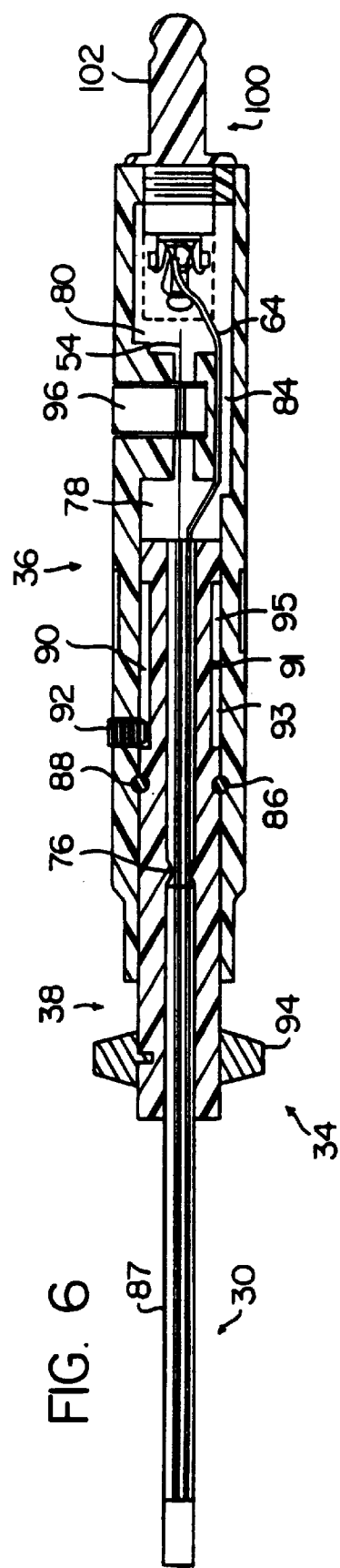

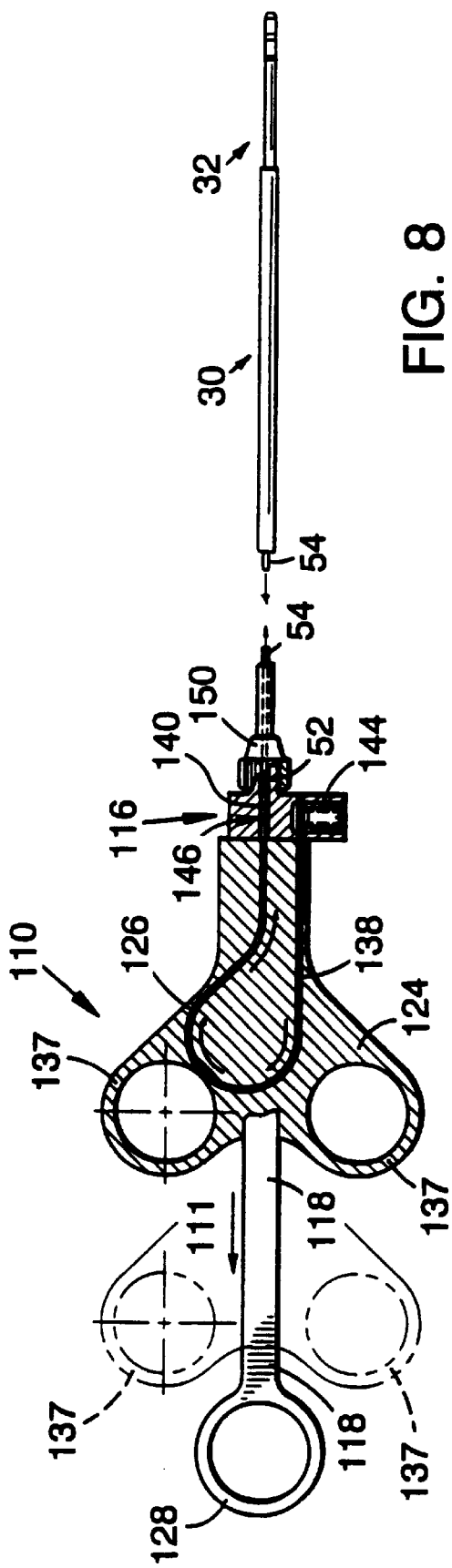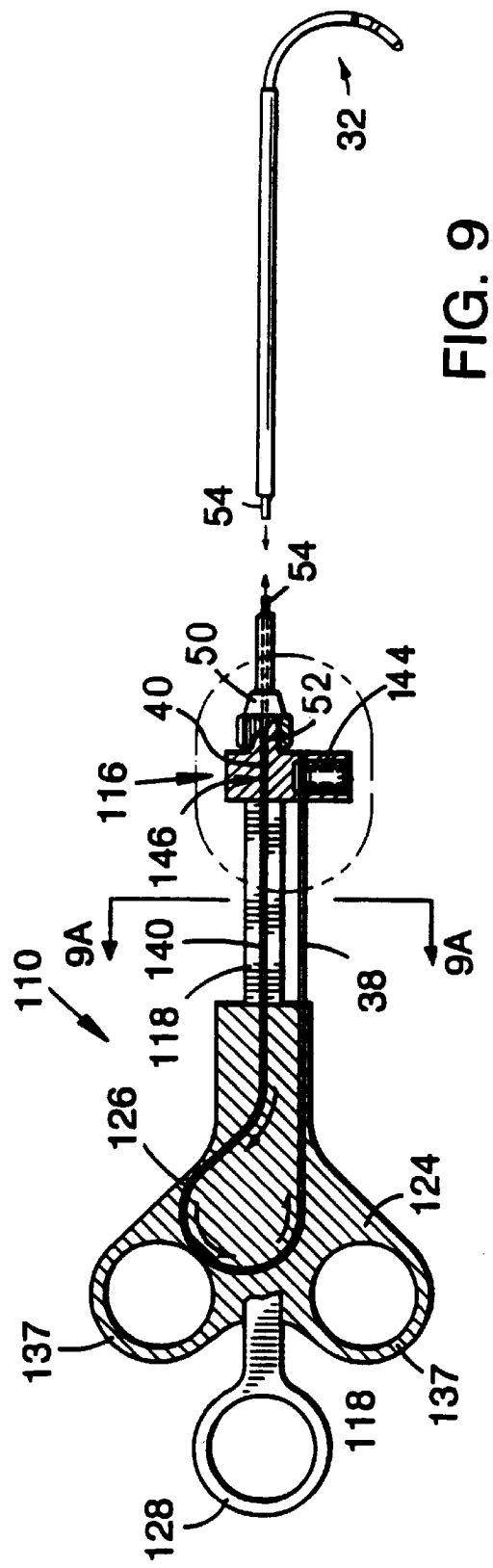

DEFLECTABLE CATHETER

CROSS REFERENCE TO RELATED APPLICATIONS

This application is a continuation of application Ser. No. 08/138,863, filed Oct. 19, 1993, now U.S. Pat. No. 5,562,619, which is a continuation-in-part of U.S. patent application Ser. No. 08/109,609 filed Aug. 19, 1993 entitled "MEDICAL DEVICE WITH IMPROVED ACTUATING HANDLE", now U.S. Pat. No. 5,376,044, which is incorporated by reference as if fully set forth herein.

BACKGROUND

This invention relates to deflectable catheters.

In order to facilitate the advancement of catheters through a body lumen (e.g., an artery) deflectable catheters have been developed. The simultaneous application of torque at the proximal end of the catheter and the ability to selectively deflect the distal tip of the catheter in a desired direction permits the physician to adjust the direction of advancement of the distal end of the catheter, as well as to position the distal portion of the catheter during e.g., an electrophysiology procedure.

A surgeon may manipulate the proximal end of the catheter to guide the catheter through a patient's vasculature. The deflection of the distal tip is typically provided by a pull wire that is attached at the distal end of the catheter and extends to a control handle that controls the application of tension on the pull wire.

In electrophysiology catheter designs it is critically important to have sufficient flexibility in the catheter shaft so that when the catheter is advanced through a blood vessel the catheter may follow the inherent curvature of the vessel without puncturing the vessel wall.

In order to maneuver around turns and bends in the vasculature, the surgeon observes the catheter fluoroscopically, and selectively deflects the tip and rotates the proximal end of the catheter shaft. However, the ability to control the precise position of the distal end of the catheter depends on the fidelity of the catheter's transmission of the forces exerted at the proximal end to the distal tip.

Without high fidelity torque transmission, the surgeon is unable to control the catheter tip and at best only delays an operating procedure, and at worst may cause the distal tip of the catheter to cause trauma to a patient.

SUMMARY

In general, the invention concerns an axially elongated steerable catheter of the type having a distal tip portion deflectable in a plane in response to a pull wire within the catheter and capable of being torqued at its proximal portion to change the rotational orientation of the tip portion about the longitudinal axis. The catheter includes: an elongated flexible outer hollow catheter body; a deflectable tip portion deflectable relative to the hollow catheter body; and a pull wire extending through the catheter to a region on the deflectable tip portion distal of the region about which the tip portion deflects. The pull wire is arranged to apply tension on the deflectable portion to produce tip deflection.

One aspect of the invention features an elongated wound wire coil extending through the hollow catheter body of the steerable catheter. The coil is constructed and arranged to enable the catheter body to withstand reactive compressive load without distortion during application of tension on the pull wire and to transmit torque along the longitudinal axis from the proximal portion to the distal tip portion of the catheter to enhance the fidelity of rotational positioning of the distal tip portion in response to change of rotational orientation of the proximal portion of the catheter. The coil is in torque-transmitting relationship with the interior of the hollow shaft substantially along the common length of the catheter body and the coil, so that when the catheter is bent within the body such that rotational drag is imposed on the catheter body that tends to cause the distal tip portion to lag the proximal portion, the coil applies torque to the hollow shaft to provide high fidelity transmission of rotational position from the proximal end to the distal portion of the catheter.

A catheter with a high fidelity transmission of torque from the proximal end to the distal tip portion permits a surgeon to precisely control the position of the catheter tip during advancement of the catheter through a body lumen, during a surgical procedure, such as electrophysiological mapping or ablation of heart tissue. The catheter achieves high torque transmission without sacrificing flexibility of the catheter shaft, so that the catheter may easily follow the inherent tortuosity of a patient's vasculature without risk of puncture to the patient's vessels.

Various embodiments of this aspect of the invention include one or more of the following features.

The coil is formed separately from the hollow catheter body. The coil includes an elongated tightly wound wire. The ratio of the clearance, between the outer surface of the coil and the internal surface of the catheter body and the transverse cross-sectional dimension of the wire in the radial direction of the coil, is less than 0.9 if the wire has a rectangular transverse cross-section, and is less than 0.6 if the wire has a circular transverse cross-section.

The proximal end of the coil is fixedly attached to the proximal end of the catheter body. The distal end of the coil is fixedly attached to the distal end of the catheter body. The coil has an outside diameter that is at most 0.010 inch less than the internal diameter of the catheter body. The surfaces are exposed and adapted for torque-transmitting contact with each other in regions where the catheter is bent. The coefficient of friction between the internal surface of the hollow catheter body and the outside surface of the coil is at least 0.3. The internal surface of the hollow catheter body is a urethane polymer, and the coil is metal. At least a distal portion of the coil includes a flattened region constructed and arranged to facilitate bending of the coil in the direction of deflection of the distal portion when tension is applied to the pull wire.

The catheter is an electrophysiology catheter further comprising at least one electrode mounted on the deflectable tip portion, and an insulated conducting wire fixedly attached to the electrode extends through the catheter to the proximal end. The conducting wire is for delivering electrical signals to and from the electrode for mapping or ablation of myocardium tissue.

The catheter is an electrophysiology catheter that further includes at least one electrode mounted on the deflectable tip portion, and an insulated conducting wire that is fixedly attached to the electrode and extends through the catheter to the proximal end. The conducting wire delivers electrical signals to and from the electrode for mapping or ablation of myocardium tissue.

The pull wire is generally coaxial with the elongated flexible hollow catheter body. The catheter body comprises a braided metal wire shaft with a polymeric coating. The proximal tip portion is constructed from a material more flexible than the catheter body. The proximal end of the deflectable tip portion is bonded to the distal end of the catheter body. A safety wire is fixedly attached to both the deflectable tip portion and the catheter body for providing flexible attachment therebetween.

In another aspect, the invention features an actuating member mounted to move relative to the catheter body. The actuating member includes a pulley surface bodily movable therewith. The pull wire is trained about the pulley surface such that movement of the actuating member a given distance, relative to the catheter body, causes the pull wire to move a substantially greater distance than the given distance, thereby applying tension on the deflectable portion to produce tip deflection.

In preferred embodiments of this aspect of the invention the pulley surface is defined by a rigid formation rigidly joined to the actuating member, about which relative sliding motion of the pull wire occurs during actuation.

In another aspect the invention features steerable catheters and especially electrophysiology catheters of the type described which include a control handle at the proximal end of the catheter. The control handle includes a housing having a piston chamber therein and a piston that has proximal and distal ends and a longitudinal bore therethrough. The piston is slidably mounted in the piston chamber. The distal end of the piston is fixedly coupled to the proximal end of the catheter body. The proximal end of the pull wire is attached to the housing at a location proximal to the piston chamber, and extends through the bore in the piston, the interior of the catheter body and into the distal lumen of the catheter tip. Longitudinal movement of the piston relative to the housing results in deflection of the catheter tip.

In another aspect, the invention features catheters of the type described which have a lubricious sheath that has a lumen with an inner diameter sized to substantially match the outer diameter of the pull wire. The sheath is disposed around the pull wire and extends from a location proximal of the proximal end of the piston chamber to a distal location spaced proximally from the distal end of the pull wire by a distance greater than or equal to the maximum operating length of longitudinal movement of the piston relative to the housing.

Other features and advantages of the invention will become apparent from the following description and from the claims.

DESCRIPTION

FIG. 3 is a side view, in partial cutaway, of the deflectable catheter in FIG. 1.

FIG. 4 is an enlarged cross-sectional side view of the distal portion of the deflectable catheter of FIG. 1.

FIG. 4A is a transverse cross-sectional view of the distal tip portion of the catheter shown in FIG. 4, taken along the line 4A—4A.

FIG. 4B is a transverse cross-sectional view of the distal end of the proximal portion of the catheter shown in FIG. 4, taken along the line 4B—4B.

FIG. 5 is a side view of a portion of a wire coil according to the invention.

FIG. 5A is a side view of a distal portion of a wire coil of the invention with a flattened region.

FIG. 5B is a cross-sectional view of the wire coil in FIG. 5A, taken along the line 5B—5B.

FIG. 6 is an enlarged cross-sectional view of the handle portion of the catheter in FIG. 1.

FIG. 8 is a side view, partially broken away, of a deflectable catheter with an actuating handle in an undeflected position.

FIG. 9 is a side view, partially broken away, of the deflectable catheter of FIG. 8 in a deflected position.

Figure 1:
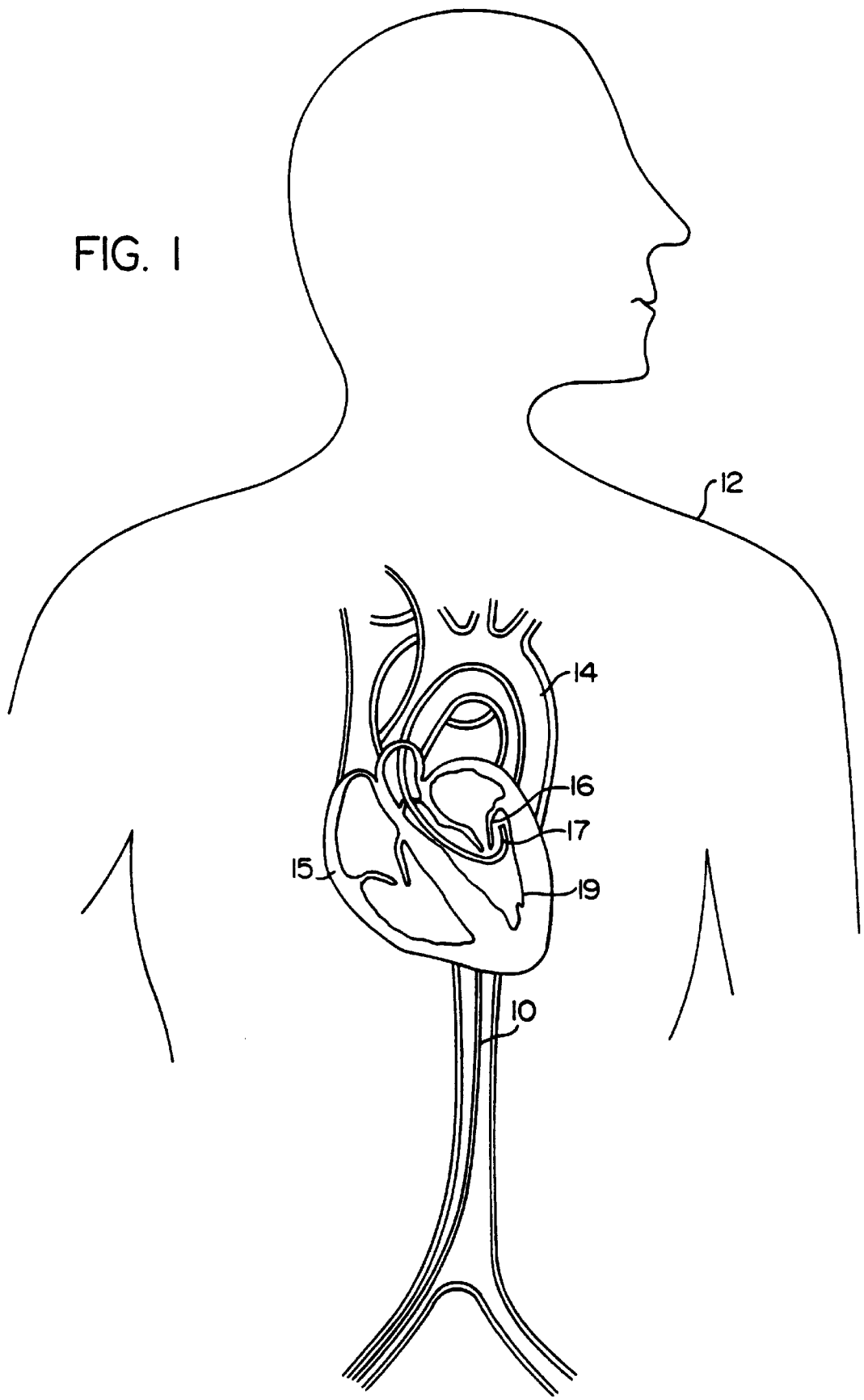
FIG. 1 is a diagrammatic illustration of a deflectable catheter of the invention disposed within the body of a patient.

Referring to FIG. 1, in an electrophysiology procedure, a deflectable catheter 10 is introduced through an introducer sheath into the right femoral artery of a patient 12 by use of the Seldinger technique (alternatively, the catheter may be introduced through the left femoral artery, or the right or left femoral veins depending upon the region of the heart to be accessed). A surgeon advances the catheter under fluoroscopic guidance through the patient's vasculature by simultaneously deflecting the distal tip of the catheter and applying torque to the proximal end of the catheter.

The catheter is advanced until the distal tip portion 16 of the catheter is positioned adjacent the region of the heart 15 (e.g., under the mitral valve 17 in left ventricle 19) that is to be mapped or ablated using electrodes that are disposed at the distal portion of the catheter. The deflectability of the catheter permits the surgeon to accurately position the electrodes against the desired portion of the heart wall.

The inventors have discovered a catheter construction in which the catheter shaft cooperates with an internal, elongated wire coil that is sized to substantially correspond to the internal diameter of the catheter shaft, and that engages with the material substance of the outer catheter body to achieve high fidelity transmission of rotational position from the proximal end to the tip of the catheter.

As the catheter is advanced through the aortic arch 14, the catheter bends significantly (e.g., about 180°) to follow the natural curvature of the aortic arch, in which case the longitudinal portion of the catheter, inside the deflected region, is under axial compression, while the outer portion is under tension. The deflected region tends to resist the transmission of torque from the proximal end to the distal tip portion 16 of the catheter which is confined within the lumen of the aorta.

When torque is applied to the proximal end of the catheter shaft, the shaft tends to rotate the entire deflected region about the proximal axis of the catheter in the direction of the applied torque. However, the catheter shaft is confined within the vessel lumen and cannot rotate without rupturing the lumen wall. The deflected region of the catheter rotates as soon as sufficient torque is generated to place into compression the longitudinal portion of the catheter that was under tension, and vice versa.

Figure 2:
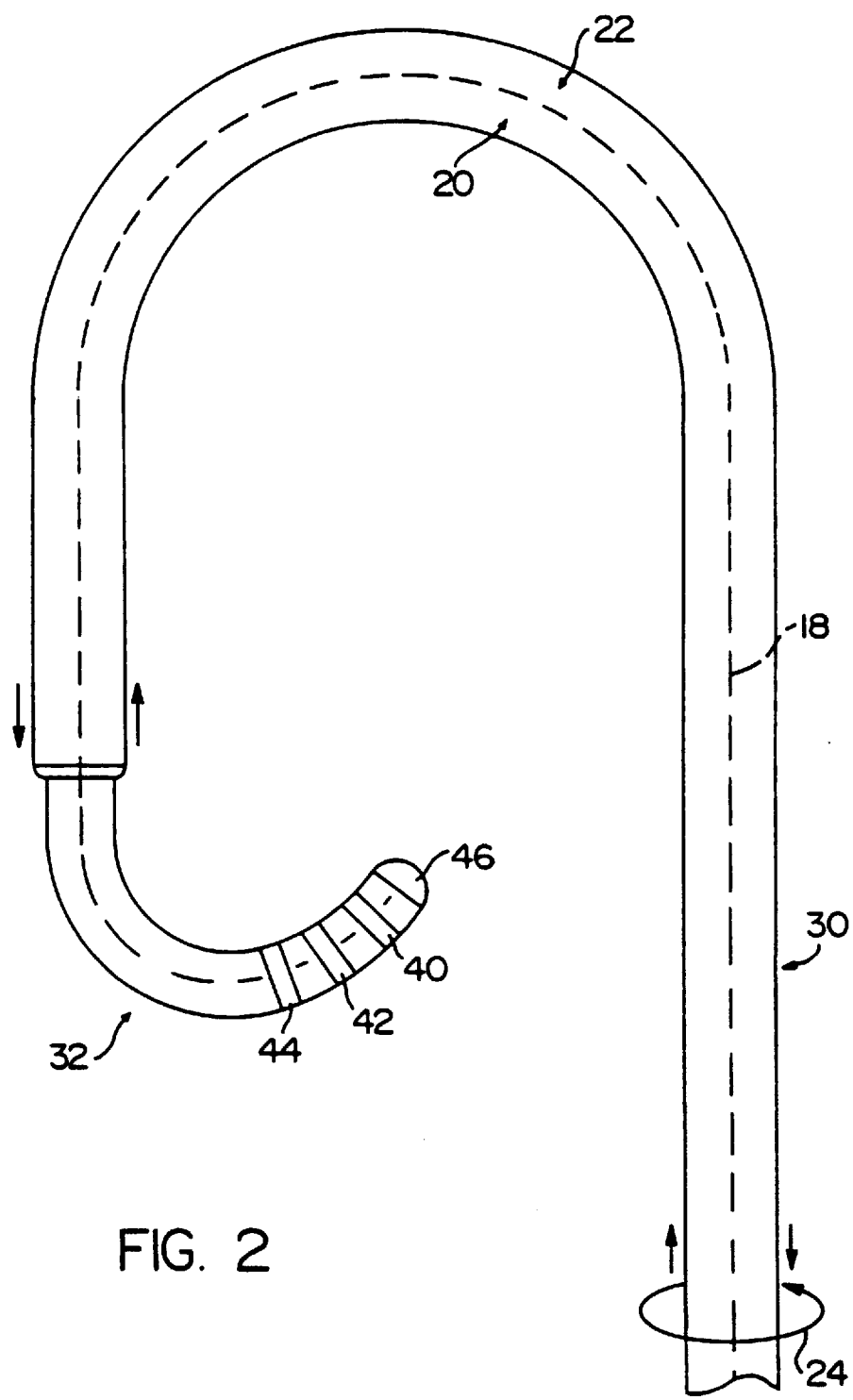
FIG. 2 is a side view of the deflectable catheter of FIG. 1 under deflection and with torque applied to its proximal end.

As shown in FIG. 2, if the deflected catheter is divided along plane 18, which passes through the axis of the catheter and is perpendicular to the plane of deflection, the portion 20 of the catheter inside the region of deflection is under axial compression, while the portion 22 is under axial tension. When torque (indicated by circular arrow 24) is applied to the proximal end of the catheter, for the tip to rotate the torque transmission of the catheter shaft must be sufficient to put portion 22 into axial compression and portion 20 into axial tension.

If the torsional strength of the catheter shaft is not sufficient to appropriately configure portions 20 and 22, the catheter shaft will tend to elastically deform and thereby store the applied torsional energy until sufficient force is generated to rotate the tip. This causes a lag in the rotation of the tip relative to the proximal end which hinders the surgeon's ability to precisely position the catheter during advancement of the catheter and during a surgical procedure.

Referring to FIG. 3, deflectable catheter 10 includes an elongated flexible outer hollow catheter body 30, a deflectable distal tip portion 32, and a handle 34 at the proximal end of the catheter. The handle includes a cylindrical housing 36 and a piston 38 that is slidably disposed within a cavity of the housing. Preferably, the handle and piston are formed from acetal, e.g., Delrin™.

The length of the catheter body is about 48 inches, while the length of the catheter tip is typically between 1½ and 3 inches. The outer diameter of the catheter body is typically about 7 French, and the outer diameter of the catheter tip is typically about 6 French. Of course, the choice of the catheter dimensions depends critically upon the anatomy of the patient and the type of procedure to be performed.

In a preferred construction, the catheter body 30 includes a stainless steel braid of counter-wound double wires with a pick count (i.e., the number of times that wires cross a unit of tube length) of about 32–34 times per inch. The stainless steel wires are braided over a polyurethane tube which is subsequently over-extruded with a polyurethane coating that bonds through the braid to the inner tubing to form a unitary structure with a hardness of about D70.

Three ring electrodes 40, 42, and 44, are disposed along the length of the catheter tip. The electrodes are mounted on the tip so that the outer surface of the electrodes form a continuous surface with the surface of the tip. A rounded tip electrode 46 is mounted on the distal end of the catheter.

Referring to FIG. 4, catheter tip 32 includes a short section of flexible tubing 47 which has a pair of non-coaxial lumens 48 and 50. Tubing 47 is formed from a polyurethane extrusion and is preferably more flexible than the catheter body 30; e.g., the tip portion preferably has a hardness of about D60.

The proximal end of the catheter tip 32 includes an outer circumferential notch 52 with an outer diameter that is sized to be snugly inserted within the lumen of the catheter body 30. The catheter tip 32 is then bonded to the catheter body with a conventional adhesive.

A pull wire 54, formed from nitinol or, e.g., stainless steel, extends from the control handle 34, through the lumen of the catheter body 30, and into lumen 48 of the catheter tip to a position near the distal end of the catheter. The pull wire 54 is crimped onto a stainless steel hypotube 56 which is welded to a short length (e.g., 0.2 inches) of stainless steel ribbon 58 to form a "T" structure. The ribbon sits within an opening 60 in the wall of catheter tip 32. The ribbon is larger than the opening which extends into lumen 48. The ribbon is bonded to the catheter tip by filling the opening with a biocompatible adhesive.

The pull wire is preferably surrounded by a teflon sheath 62. The sheath extends from a location near the proximal end of the piston chamber to a distal location that is spaced proximally of the distal end of the pull wire by at least a distance equal to the maximum operating length of longitudinal movement of the piston relative to the housing (e.g., ½ to ¾ inch). The sheath provides lubricity for the movement of the pull wire, and also serves to maintain the pull wire in generally coaxial relation with the catheter body 30.

Electrode lead wires 64 extend from the handle 34, through the catheter body and into lumen 50 of the catheter tip. The lead wires are soldered to the electrodes in a conventional manner.

A proximal safety wire 66 is attached to the tip electrode 46 and extends to a short length (e.g., ¾ inch) of teflon tubing 68. The proximal safety wire is folded between the outer surface of notch 52 and the inside surface of the distal end of the catheter body 30. The proximal safety wire is further wedged between the proximal edge of the catheter tip and the distal edge of the teflon tubing 68. The outer surface of the teflon tubing is glued to the inside surface of the catheter body.

A second safety wire 70 is attached to the tip electrode 46 and extends to the ribbon 58. The second safety wire is folded on itself, distally of the ribbon, to form a loop which is potted in the opening 60, and glued in place with the biocompatible adhesive described above.

A closely wound spring coil 72, shown in greater detail in FIG. 5, is disposed within the lumen of the catheter body 30. The proximal end of the teflon tubing abuts against the distal end of coil 72. The spring coil 72 has an inside diameter of about 0.038 inch and an outside diameter of about 0.058 inch, and fits closely within the inside diameter of the shaft 30, which is about 0.059–0.062 inch. The coil is made from e.g., 302 stainless steel wire that may have a circular cross-section, although a wire with a rectangular cross-section may be preferable. The coil extends distally from the proximal tip of catheter body 30 to near the teflon tube 68. The coil may also be fabricated from other spring-like materials, such as nitinol.

During fabrication of catheter 10, the catheter body 30 slides over a tip assembly that includes catheter tip 32 with the ring and tip electrodes, the pull wire, the safety wires and the electrical lead wires. All of the wires are subsequently pulled through catheter body 30. The spring coil slips over the proximal end of the pull wire and over the electrical lead wires and into the catheter body.

Figure 7:
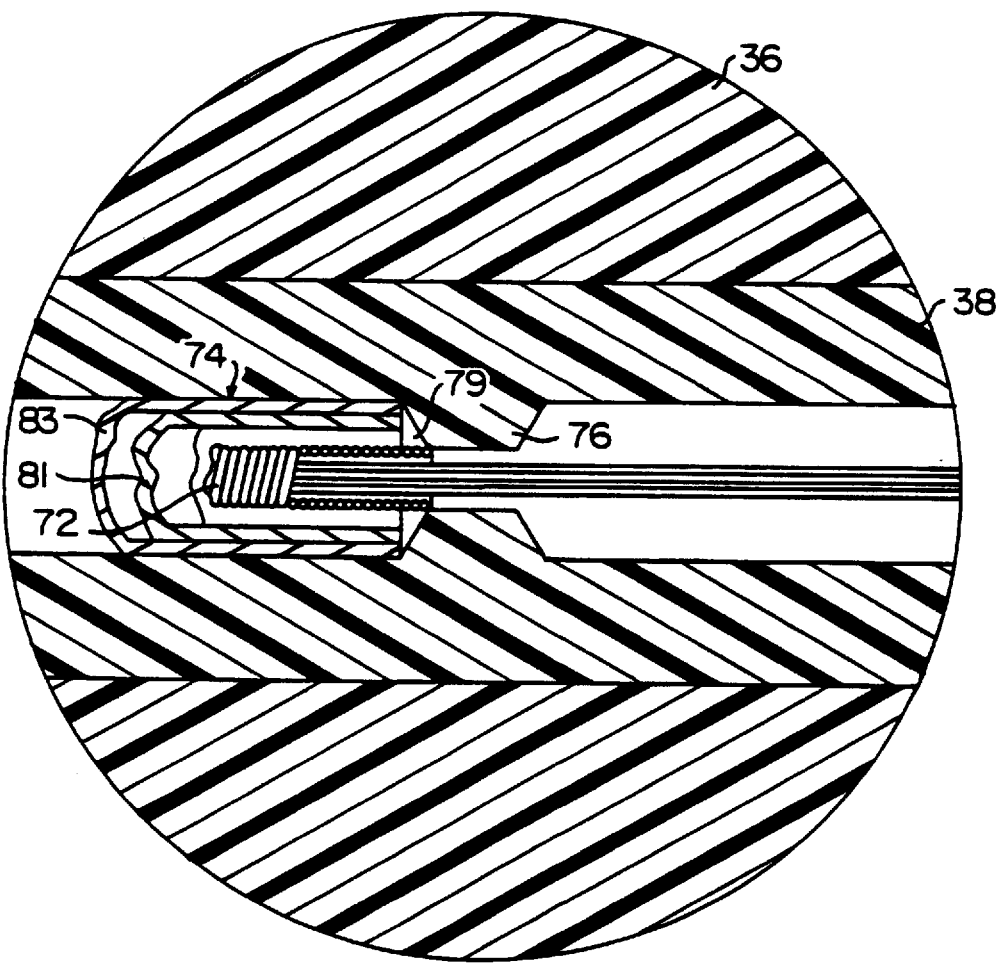
FIG. 7 is a further enlarged cross-sectional view of a region of the handle portion of the catheter shown in FIG. 5.

As shown in FIGS. 6 and 7, the proximal end of the catheter body 30, with the coil disposed therein, fits with a bore 74 inside the piston 38 and abuts against a lip 76 that consists of a region of the piston in which the diameter of piston bore 74 is reduced. The catheter body is attached at the proximal end to the piston using, e.g., a cyanoacrylate adhesive 79.

The coil structure provides a highly efficient transmission of torque (e.g., around curves) because the direction of the applied torque substantially corresponds to the incompressible axis of the coiled wire.

In a presently preferred embodiment, the coil is attached to the catheter body 30, which allows a certain amount of stretch in the portion of the coils on the outside portion of a bent region of the catheter body, thereby achieving a high flexibility while providing the efficient torque-transmitting capability of the coil. In other words, as the catheter body is bent e.g., through the aortic arch, the upper part of the coil opens up to maintain the flexibility, but the inner portion of the coil is tight in compression. In this position, the coil, together with the catheter body, are able to transmit torsional and tensile forces exerted on the proximal end of the catheter.

The spring coil 72 cooperates with the catheter body 30 in a self-correcting, torque-transmitting relationship. When the catheter is disposed within a body lumen (e.g., an artery), the inherent curvature of the body lumen causes the outer surface of the steel coil to frictionally engage the internal polyurethane surface of the catheter body 30. This frictional engagement permits the coil to cooperatively transmit torque with the catheter body from the proximal end to the distal end of the catheter.

The coefficient of friction of the internal surface of the catheter body is therefore a critical design choice for certain preferred embodiments of the catheter. The coefficient of friction of the internal surface of the catheter body should be at least about 0.3 to permit adequate torque transmission between the coil and the catheter body. The coil should be appropriately sized to achieve optimal engagement between the outside surface of the coil and the internal surface of the catheter body. The outside diameter of the coil should be at most 0.010 inch less than the inside diameter of the catheter body for a catheter body with an internal diameter of about 0.063 inch.

In addition, the close fit between the outer diameter of the coil and the inner diameter of the catheter body prevents the individual coils of the spring coil from slipping relative to one another when the catheter is bent, and thus prevents the coil from tending to buckle under the compressive loads associated with the advancement of the catheter and with the deflection of the distal tip portion.

In this regard, a critical feature of preferred embodiments of the catheter design is the ratio of the clearance (i.e., the difference between the inner diameter of the shaft and the outer diameter of the coil) to the wire diameter of the coil. The ratio of the clearance to the coil wire diameter is preferably less than about 0.9 for wires with a rectangular cross-section, while for coil wires with a circular cross-section, the ratio of the clearance to wire diameter is preferably less than about 0.6.

In other words, the coil, in a sense, compensates for the low compressive strength of the catheter body, while the catheter body compensates for the low shear strength of the coil, to provide a catheter that permits a surgeon to precisely control the position of the distal tip portion of the catheter.

While in the presently preferred embodiment the proximal end only of the coil is securely attached to the catheter body, it is within the scope of broader aspects of the invention to attach either the distal or proximal ends of the coil to the catheter body. It is also within the scope of broader aspects of the invention to construct the coil integrally with or adhered to the catheter body.

In certain preferred embodiments the distal portion (e.g., the distal 10 cm) of the coil has a flattened region 75, as shown in FIGS. 5A and 5B. The flat consists of a portion of the coil that has been ground away by conventional means to cause a preferential region of weakness in the distal portion of the coil. Up to about half of the diameter of the wire of the coil may be ground away, as shown in FIG. 5B. The coil is securely positioned in the catheter body so that the outer surface of flattened region is facing the direction that the distal portion deflects in response to tension applied to the pull wire (i.e., the flat would be facing toward the bottom of the page in FIG. 3, or alternatively would be facing toward the top of the page in FIG. 4). This flattened portion facilitates bending of the catheter in the preferred deflection direction.

Referring to FIG. 7, inner and outer layers 81 and 83, respectively, of teflon shrink tubing surround the proximal end of the catheter shaft. The inner tubing 81 extends to location 85 on the catheter body, while the outer tubing 83 extends to a location 87, proximal of location 85.

The handle includes a cylindrical housing 36 that has a piston chamber 78 at the proximal end and a connector chamber 80 at the proximal end. There is an axial passage 82 and an offset passage 84 connecting the piston and connector chambers. The housing is generally symmetrical about its longitudinal axis, allowing the handle to be freely rotated without altering convenience or quality of control.

The piston includes a circumferential O-ring notch 86 that carries an O-ring 88 to provide a watertight seal between the piston and the wall of the piston chamber.

The piston includes an upper slot 90 that extends along a portion of its length proximal of the O-ring notch. A set screw 92 extends from the wall of the housing into the slot. The set screw restricts the longitudinal movement of the piston by engaging the proximal and distal ends of the slot.

A lower slot 91 is disposed on the opposite side of the piston as the upper slot. Within the lower slot are two adjacent, short (e.g., ⅜ inch long) pieces of teflon tubing that provide a lubricious surface to facilitate axial movement of the piston with respect to the handle housing.

The distal end of the piston extends beyond the distal end of the housing so that it may be manually controlled by a user. An annular thumbrest 94 is attached to the distal end of the piston to facilitate axial movement of the piston.

The pull wire extends through the axial bore of the piston and is attached to the housing by an anchor 96. The anchor extends into a transverse hole in the portion of the housing between the connector and the piston chambers. The anchor blocks the axial passage, but not the offset passage. The anchor is rotatable within the hole, but fits snugly so that it does not rotate freely.

The anchor includes a transversely extending hole that may be rotated into alignment with the axial passage. To secure the pull wire to the anchor, the pull wire is passed through the axial passage and the transversely extending hole in the anchor, and the anchor is rotated, by means of a flat screw driver slot 98, to wedge the pull wire between the anchor and the wall of the housing. Tension on the pull wire may be adjusted by rotation of the anchor.

In use, the catheter tip may be curved or bent to steer the tip by gripping the control handle housing and moving the piston distally out of the piston chamber. Because the catheter body is attached to the piston and the pull wire is attached to the housing, pushing distally on the thumbrest causes movement of the pull wire with respect to the catheter body and tip, thereby pulling the catheter tip proximally toward the handle. Because the pull wire is attached to one side of the catheter tip, the tip bends preferentially in the direction of attachment (i.e., as shown by the dotted line in FIG. 3) to accommodate the force exerted on it.

By maintaining the pull wire in coaxial relation with the catheter body, the length of the pull wire and on-axis length of the catheter body are the same, whether the catheter body extends around a curve or not. In this arrangement, less energy is required for rotation of the catheter tip. This allows the tip to be more responsive to rotation of the handle and therefore more easily controlled.

Electrode lead wires 64 extend from the catheter body proximally through the axial bore of the piston and connector chambers, and into the connector chamber. Preferably a teflon sheath surrounds and protects the lead wires in the piston chamber. Within the connector chamber, the lead wires and the surrounding sheath are bowed slightly to provide slack as the catheter is manipulated.

In the connector chamber, the lead wires are connected to a rotary connector 100. The rotary connector includes a conventional cylindrical male plug 102 (e.g., a NEXUS™ plug) that extends proximally from the handle housing. The plug has a series of terminals along its length, each of which is connected to a separate lead wire within the connector chamber. These terminals operate independently of each other and allow separate electrical signals to be transmitted through the connector simultaneously.

Other embodiments are within the scope of the claims. For example, handle 34 may be replaced with a snare handle 110, shown in FIG. 8, and described in U.S. Ser. No. 08/109,609, filed on Aug. 19, 1993 by Craig R. Kline, assigned to the present assignee and incorporated herein fully by reference.

Referring to FIGS. 8 and 10, the snare handle advances and withdraws pull wire 54 within catheter body 30, which is bonded to the distal end 150 of the handle body 118. The proximal end of pull wire 54 is fixed to nose 116 of handle body 118. By pulling back on the finger handle 137 relative to the handle body 118 in the distal direction indicated by arrow 111, the distal tip portion 32 becomes deflected from the straight position shown in FIG. 8 to the deflected position shown in FIG. 9.

Handle body 118 is preferably a single injection molded component composed of nylon or other resilient material having legs 130 which define channel 132. A thumb ring 128 is located at one end of handle body 118 to enable an operator to control it, and, if desired, thumb ring 118 may be rotatable.

Figure 9A:
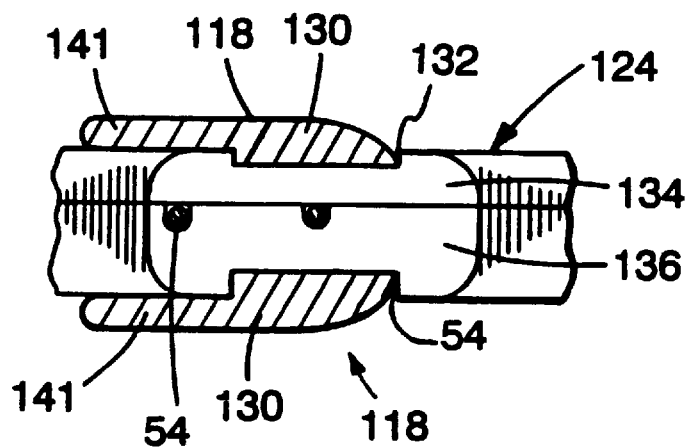
FIG. 9A is a transverse cross-sectional view on an enlarged scale taken along the line 9A—9A of FIG. 8.
Figure 9B:
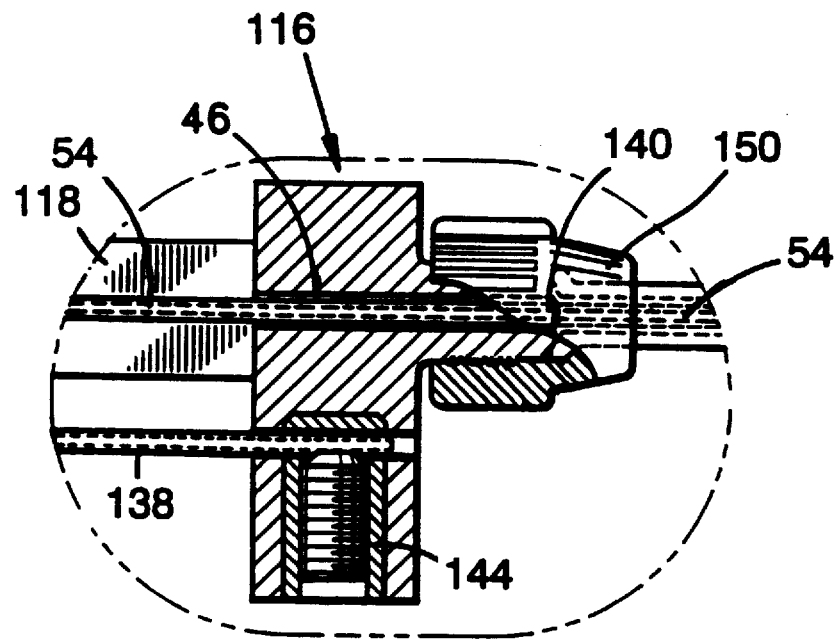
FIG. 9B is a cross-sectional view on an enlarged scale of the portion of the device in FIG. 8, encircled by dotted lines.

Referring more specifically to FIG. 10, actuating member 124 is slidably disposed on handle body 118 between legs 130 in channel 132. Actuating member 124 preferably is made of nylon, Delrin, or any suitable polymeric injection molded material. Actuating member 124 may be manufactured as a clam shell with top half 134 and bottom half 136 separately injection molded and later joined by melting, snap fitting, through the application of an adhesive such as cyanoacrylate, or clamped together by legs 130 of handle body 118. As shown in FIGS. 8 and 9, actuating member 124 preferably has two finger loops disposed on opposite sides of handle body 118 for engagement by fingers of an operator.

Pulley surface 126 is disposed on actuating member 124 and may be rotary or stationary. In a preferred embodiment, pulley surface 126 defines a rigid, semicircular track 156 integral with actuating member 124 and has a cross section only slightly larger than pull wire 54 to prevent pull wire 54 from buckling under compressive force.

A biocompatible silicon type lubricant may be used to reduce friction on pulley surface 126 in embodiments of the invention employing both fixed and rotatable pulley surfaces.

The pulley advantage of pulley surface 126, which is in direct contact with pull wire 54, allows the operator to achieve the desired two-to-one activation ratio in one-handed operation, while the absence of intervening parts provides the tactile feeling previously only available in handles with a one to one activation ratio.

Referring now to FIG. 11, pull wire 54 passes through nose 116 of handle body 118 around pulley surface 126 on actuating member 24, and back to nose 16 where the end of pull wire 54 is fixed to nose 116. Pull wire 54 is confined throughout its entire pathway within medical device 110 to prevent columnar buckling. Preferably, cannulae 138 and 140 are used to confine pull wire 54 between nose 116 and actuating member 124. Pull wire 54 is connected, by soldering or any other method, to one end of cannula 138. This end is attached to body 118 by set screw 142 disposed in can 144 on nose 116. The other end of cannula 138 is telescopically disposed within actuating member 124. Similarly, cannula 140 has one end attached to actuating member 124 and the other end telescopically disposed within aperture 146 in nose 116.

Cannulae 138 and 140 are preferably stainless steel tubes which confine pull wire 54 and allow about five thousandths of an inch clearance between the inside wall of the tube and the pull wire. The cannula wall is preferably about two thousandths of an inch thick. The exterior of cannula 138 and 140 may be coated with an insulator such as nylon to prevent a person operating the medical device from being shocked. Alternatively, as shown in FIG. 10, guard 141 (a part of body 118 which extends outward from legs 130 to cover cannula 138) may be included for this same purpose.

Actuation of the snare handle causes pull wire 54 to move about pulley surface 126, through cannula 140 and out nose 116. Due to the pulley advantage of pulley surface 126, movement of actuating member 124 a given distance 162 results in translation of pull wire 54 twice the given distance. This two-fold increase in the cable stroke relative to movement of actuating member 124 permits a nurse with small hands to operate the snare handle with one hand.

What is claimed is:

1. An axially elongated steerable catheter comprising:
   an elongated flexible outer hollow catheter body defining a proximal portion and a longitudinal axis;
   a deflectable tip portion deflectable relative to said hollow catheter body;
   a pull wire extending through said hollow catheter body to a region on said deflectable tip portion distal of the region about which said deflectable tip portion deflects, said pull wire arranged to apply tension on said deflectable portion to produce tip deflection tip; and
   an elongated wound wire coil extending through the hollow catheter body,
   said coil constructed and arranged to enable said hollow catheter body to withstand reactive compressive load without distortion during application of tension on said pull wire and to transmit torque along the longitudinal axis from the proximal portion to the deflectable tip portion of said catheter to enhance the fidelity of rotational positioning of the deflectable tip portion in response to change of rotational orientation of the proximal portion of the hollow catheter body, said coil being in torque-transmitting relationship with the interior of said hollow catheter body substantially along the common length of the hollow catheter body and the coil, so that when said catheter is bent within the body such that rotational drag is imposed on said hollow catheter body that tends to cause the deflectable tip portion to lag the proximal portion, said coil applies torque to said hollow catheter body to provide high fidelity transmission of rotational position from the proximal end to said deflectable tip portion of said catheter.

2. The steerable catheter of claim 1 wherein said coil is formed separately from said hollow catheter body, said coil comprises an elongated tightly wound wire, and the ratio of the clearance between the outer surface of the coil and the internal surface of the hollow catheter body and the transverse cross-sectional dimension of said wire in the radial direction of said coil, is less than 0.9.

3. The steerable catheter of claim 2 wherein the tightly wound wire comprises wire with a circular cross-section and said ratio of said clearance to the diameter of said wire is less than 0.6.

4. The catheter of claim 2 wherein said surfaces are exposed and adapted for torque-transmitting contact with each other in regions where the hollow catheter body is bent, the coefficient of friction of the internal surface of said hollow catheter body being at least about 0.3.

5. The catheter of claim 4 wherein the internal surface of said hollow catheter body is a urethane polymer, and the outside surface of said coil is metal.

6. The catheter of claim 1 wherein the proximal end of said coil is fixedly attached to the proximal end of said hollow catheter body.

7. The catheter of claim 1 wherein the distal end of said coil is fixedly attached to the distal end of said hollow catheter body.

8. The catheter of claim 1 wherein said coil has an outside diameter that is at most 0.010 inch less than the internal diameter of said hollow catheter body.

9. The hollow catheter body of claim 1 wherein said catheter is an electrophysiology catheter further comprising at least one electrode mounted on said deflectable tip portion, and an insulated conducting wire fixedly attached to said electrode extends through said hollow catheter body to the proximal end, said conducting wire constructed to deliver electrical signals to and from said electrode for mapping or ablation of myocardium tissue.

10. The catheter of claim 1 wherein said pull wire is generally coaxial with said hollow catheter body.

11. An axially elongated steerable catheter, comprising:

an elongated flexible outer hollow catheter body defining a proximal portion and a longitudinal axis;

a deflectable tip portion deflectable relative to said hollow catheter body;

a pull wire extending through said hollow catheter body to a region on said deflectable tip portion distal of the region about which said deflectable tip portion deflects, said pull wire arranged to apply tension on said deflectable tip portion to produce tip deflection; and an elongated wound wire coil extending through the hollow catheter body formed separately from said hollow catheter body from an elongated tightly wound wire having a rectangular cross-section, said coil constructed and arranged to enable said hollow catheter body to withstand reactive compressive load without distortion during application of tension on said pull wire and to transmit torque along the longitudinal axis from the proximal portion to the deflectable tip portion of said catheter to enhance the fidelity of rotational positioning of the deflectable tip portion in response to change of rotational orientation of the proximal portion of the hollow catheter body, said coil being in torque-transmitting relationship with the interior of said hollow catheter body substantially along the common length of the catheter hollow body and the coil so that when said hollow catheter body is bent within the body such that rotational drag is imposed on said hollow catheter body that tends to cause the deflectable tip portion to lag the proximal portion, said coil applies torque to said hollow catheter body to provide high fidelity transmission of rotational position from the proximal end of said hollow catheter body to said deflectable tip portion of said hollow catheter body;

whereby the ratio of the clearance between the outer surface of the coil and the internal surface of the hollow catheter body and the transverse cross-sectional dimension of said wire in the radial direction of said coil, being less than 0.9.

12. A axially elongated steerable catheter, comprising:

an elongated flexible outer hollow catheter body defining a proximal portion and a longitudinal axis and being formed from a braided metal wire shaft with a polymeric coating;

a deflectable tip portion deflectable relative to said hollow catheter body;

a pull wire extending through said hollow catheter body to a region on said deflectable tip portion distal of the region about which said deflectable tip potion deflects, said pull wire arranged to apply tension on said deflectable portion to produce tip deflection tip; and an elongated wound wire coil extending through the hollow catheter body;

said coil constructed and arranged to enable said hollow catheter body to withstand reactive compressive load without distortion during application of tension on said pull wire and to transmit torque along the longitudinal axis from the proximal portion to the deflectable tip portion of said catheter to enhance the fidelity of rotational positioning of the deflectable tip portion in response to change of rotational orientation of the proximal portion of the hollow catheter body, said coil being in torque-transmitting relationship with the interior of said hollow catheter body substantially along the common length of the hollow catheter body and the coil, so that when said hollow catheter body is bent within the body such that rotational drag is imposed on said hollow catheter body that tends to cause the deflectable tip portion to lag the proximal portion, said coil applies torque to said hollow catheter body to provide high fidelity transmission of rotational position from the proximal end to said deflectable tip portion of said hollow catheter body.

13. An axially elongated steerable catheter, comprising:

an elongated flexible outer hollow catheter body defining a proximal portion and a longitudinal axis;

a deflectable tip portion deflectable relative to said hollow catheter body;

a pull wire extending through said hollow catheter body to a region on said deflectable tip portion distal of the region about which said deflectable tip potion deflects, said pull wire arranged to apply tension on said deflectable tip portion to produce tip deflection; and an elongated wound wire coil extending through the hollow catheter body, at least a distal portion of said coil including a flattened region constructed and arranged to facilitate bending of said coil in the direction of deflection of said deflectable tip portion when tension is applied to said pull wire, said coil constructed and arranged to enable said hollow catheter body to withstand reactive compressive load without distortion during application of tension on said pull wire and to transmit torque along the longitudinal axis from the proximal portion to the deflectable tip portion of said catheter to enhance the fidelity of rotational positioning of the deflectable tip portion in response to change of rotational orientation of the proximal portion of the hollow catheter body, said coil being in torque-transmitting relationship with the interior of said hollow catheter body substantially along the common length of the catheter body and the coil, so that when said hollow catheter body is bent within the body such that rotational drag is imposed on said hollow catheter body that tends to cause the deflectable tip portion to lag the proximal portion, said coil applies torque to said hollow body to provide high fidelity transmission of rotational position from the proximal end to said deflectable portion of said hollow catheter body.

14. An axially elongated steerable catheter, comprising:

an elongated flexible outer hollow catheter body defining a proximal portion and a longitudinal axis;

a deflectable tip portion deflectable relative to said hollow catheter body;

a pull wire extending through said hollow catheter body to a region on said deflectable tip portion distal of the region about which said deflectable tip potion deflects, said pull wire arranged to apply tension on said deflectable tip portion to produce tip deflection;

an elongated wound wire coil extending through the hollow catheter body, said coil constructed and arranged to enable said hollow catheter body to withstand reactive compressive load without distortion during application of tension on said pull wire and to transmit torque along the longitudinal axis from the proximal portion to the deflectable tip portion of said catheter to enhance the fidelity of rotational positioning of the deflectable tip portion in response to chance of rotational orientation of the proximal portion of the hollow catheter body, said coil being in torque-transmitting relationship with the interior of said hollow body substantially along the common length of the hollow catheter body and the coil, so that when said hollow catheter body is bent within the body such that rotational drag is imposed on said hollow catheter body that tends to cause the deflectable tip portion to lag the proximal portion, said coil applies torque to said hollow catheter body to provide high fidelity transmission of rotational position from the proximal end to said deflectable tip portion of said hollow catheter body; and a control handle at the proximal end of the hollow catheter body including
  a housing having a piston chamber therein, and
  a piston having proximal and distal ends and a longitudinal bore therethrough, said piston being slidably mounted in the piston chamber, said distal end of said piston being fixedly coupled to the proximal end of said hollow catheter body,
  the proximal end of said pull wire being attached to said housing at a location proximal to the piston chamber, said pull wire extending through the bore on the piston, the interior of the hollow catheter body and into the distal lumen of the deflectable tip portion, whereby longitudinal movement of the piston relative to the housing results in deflection of the deflectable tip portion.

15. An axially elongated steerable catheter, comprising:

an elongated flexible outer hollow catheter body defining a proximal portion and a longitudinal axis;

a deflectable tip portion deflectable relative to said hollow catheter body;

a pull wire extending through said hollow catheter body to a region on said deflectable tip portion distal of the region about which said deflectable tip potion deflects, said pull wire arranged to apply tension on said deflectable tip portion to produce tip deflection;

an elongated wound wire coil extending through the hollow catheter body, said coil constructed and arranged to enable said hollow catheter body to withstand reactive compressive load without distortion during application of tension on said pull wire and to transmit torque along the longitudinal axis from the proximal portion to the deflectable tip portion of said catheter to enhance the fidelity of rotational positioning of the deflectable tip portion in response to change of rotational orientation of the proximal portion of the hollow catheter body, said coil being in torque-transmitting relationship with the interior of said hollow body substantially along the common length of the hollow catheter body and the coil, so that when said hollow catheter body is bent within the body such that rotational drag is imposed on said hollow catheter body that tends to cause the deflectable tip portion to lag the proximal portion, said coil applies torque to said hollow catheter body to provide high fidelity transmission of rotational position from the proximal end to said deflectable tip portion of said hollow catheter body; and a handle attached to the proximal portion of said hollow catheter body, and constructed for one-handed operation, said handle having a movable member attached to the proximal portion of said pull wire, said hollow handle being characterized in that movement of said member a given distance relative to said catheter body, causes said pull wire to move a substantially greater distance than said given distance, to enhance the range of tip deflection.

16. The catheter of claim 15 wherein said movable member includes a pulley surface bodily movable therewith, said pull wire being trained about said pulley surface.

17. The catheter of claim 16 wherein said pulley surface is defined by a rigid formation rigidly joined to said movable member, about which relative sliding motion of said pull wire occurs during actuation.

18. An axially elongated steerable catheter, comprising:

an elongated flexible outer hollow catheter body defining a proximal portion and a longitudinal axis, a deflectable tip portion deflectable relative to said hollow catheter body, the proximal end of said deflectable tip portion being bonded to the distal end of said hollow catheter body;

said proximal end of said deflectable tip portion being constructed from a material more flexible than said hollow catheter body;

a pull wire extending through said hollow catheter body to a region on said deflectable tip portion distal of the region about which said deflectable tip portion deflects, said pull wire arranged to apply tension on said deflectable tip portion to produce tip deflection;

an elongated wound wire coil extending through the hollow catheter body, said coil constructed and arranged to enable said hollow catheter body to withstand reactive compressive load without distortion during application of tension on said pull wire and to transmit torque along the longitudinal axis from the proximal portion to the deflectable tip portion of said catheter to enhance the fidelity of rotational positioning of the deflectable tip portion in response to change of rotational orientation of the proximal portion of the hollow catheter body, said coil being in torque-transmitting relationship with the interior of said hollow catheter body substantially along the common length of the hollow catheter body and the coil, so that when said hollow catheter body is bent within the body such that rotational drag is imposed on said hollow catheter body that tends to cause the deflectable tip portion to lag the proximal portion, the coil applies torque to said hollow body to provide high fidelity transmission of rotational position from the proximal end to said deflectable tip portion of said hollow catheter body; and a safety wire fixedly attached to both said deflectable tip portion and said catheter body for providing flexible attachment therebetween.

19. An axially elongated steerable electrophysiology catheter of the type having a distal tip portion deflectable in a plane in response to a pull wire within the catheter and capable of being torqued at its proximal portion to change the rotational orientation of the tip portion about the longitudinal axis, said catheter comprising:

an elongated flexible outer hollow catheter body;

a deflectable tip portion deflectable relative to said hollow catheter body;

a pull wire extending through said hollow catheter body to a region on said deflectable tip portion distal of the region about which said deflectable tip portion deflects, said pull wire arranged to apply tension on said deflectable portion to produce tip deflection;

a handle attached to the proximal portion of said hollow catheter body, said handle having a movable member attached to the proximal portion of said pull wire, said handle being characterized in that movement of said member a given distance relative to said hollow catheter body causes said pull wire to move a substantially greater distance than said given distance, thereby applying tension on said deflectable portion to produce tip deflection;

at least one electrode mounted on said deflectable tip portion; and an insulated conducting wire fixedly attached to said electrode extending through said catheter to the proximal end, said conducting wire constructed to deliver electrical signals to and from said electrode for mapping or ablation of myocardium tissue.

20. A catheter, comprising:

a substantially elongate, flexible and hollow catheter body defining a proximal portion, a distal portion and a longitudinal axis;

a deflectable tip portion associated with the distal portion of the catheter body and deflectable relative to the catheter body;

a pull wire extending through the catheter body to a region of the deflectable tip portion, the pull wire being arranged to apply tension to the deflectable tip portion to produce tip portion deflection; and an elongate wire coil, extending through the catheter body and adapted to transmit torque to the catheter body in response to a change in rotational orientation of the proximal portion of the catheter body when the catheter body is bent;

wherein the catheter body defines an interior surface, the coil defines an exterior surface and the distance between the interior surface of the catheter body and the exterior surface of the coil is at most 0.005 inch when the coil and catheter body are coaxial.

21. A catheter, comprising:

a substantially elongate, flexible and hollow catheter body defining a proximal portion, a distal portion and a longitudinal axis;

a deflectable tip portion associated with the distal portion of the catheter body and deflectable relative to the catheter body;

a pull wire extending through the catheter body to a region of the deflectable tip portion, the pull wire being arranged to apply tension to the deflectable tip portion to produce tip portion deflection; and an elongate wire coil, extending through the catheter body and adapted to transmit torque to the catheter body in response to a change in rotational orientation of the proximal portion of the catheter body when the catheter body is bent;

wherein the coil comprises a wire having a rectangular cross-section and defines an exterior surface, the catheter body defines an interior surface, and the ratio of clearance between the exterior surface of the coil and the interior surface of the catheter body to the transverse cross-sectional dimension of the wire in the radial direction of said coil, is less than 0.9.

22. A catheter, comprising:

a substantially elongate, flexible and hollow catheter body defining a proximal portion, a distal portion and a longitudinal axis;

a deflectable tip portion associated with the distal portion of the catheter body and deflectable relative to the catheter body;

a pull wire extending through the catheter body to a region of the deflectable tip portion, the pull wire being arranged to apply tension to the deflectable tip portion to produce tip portion deflection; and an elongate wire coil, extending through the catheter body and adapted to transmit torque to the catheter body in response to a change in rotational orientation of the proximal portion of the catheter body when the catheter body is bent;

wherein the coil comprises a wire having a circular cross-section and defines an exterior surface, the catheter body defines an interior surface, and the ratio of clearance between the exterior surface of the coil and the interior surface of the catheter body to the diameter of the wire, is less than 0.6.

23. A catheter, comprising:

a substantially elongate, flexible and hollow catheter body defining an interior surface, a proximal portion, a distal portion and a longitudinal axis;

a deflectable tip portion associated with the distal portion of the catheter body and deflectable relative to the catheter body;

a pull wire extending through the catheter body to a region of the deflectable tip portion, the pull wire being arranged to apply tension to the deflectable tip portion to produce tip portion deflection; and a spring coil defining an exterior surface extending through the catheter body, the exterior surface of the spring coil and the interior surface of the catheter body defining a predetermined distance therebetween, the predetermined distance being such that the spring coil will transmit torque to the catheter body in response to a change in rotational orientation of the proximal portion of the catheter body when the catheter body is bent;

wherein the distance between the interior surface of the catheter body and the exterior surface of the coil is at most 0.005 inch when the coil and catheter body are coaxial.

24. A catheter, comprising:

a substantially elongate, flexible and hollow catheter body defining an interior surface, a proximal portion, a distal portion and a longitudinal axis;

a deflectable tip portion associated with the distal portion of the catheter body and deflectable relative to the catheter body;

a pull wire extending through the catheter body to a region of the deflectable tip portion, the pull wire being arranged to apply tension to the deflectable tip portion to produce tip portion deflection; and a spring coil defining an exterior surface extending through the catheter body, the exterior surface of the spring coil and the interior surface of the catheter body defining a predetermined distance therebetween, the predetermined distance being such that the spring coil will transmit torque to the catheter body in response to a change in rotational orientation of the proximal portion of the catheter body when the catheter body is bent;

wherein the coil comprises a wire having a rectangular cross-section and the ratio of clearance between the exterior surface of the coil and the interior surface of the catheter body to the transverse cross-sectional dimension of the wire in the radial direction of said coil, is less than 0.9.

25. A catheter, comprising:

a substantially elongate, flexible and hollow catheter body defining an interior surface, a proximal portion, a distal portion and a longitudinal axis;

a deflectable tip portion associated with the distal portion of the catheter body and deflectable relative to the catheter body;

a pull wire extending through the catheter body to a region of the deflectable tip portion, the pull wire being arranged to apply tension to the deflectable tip portion to produce tip portion deflection; and a spring coil defining an exterior surface extending through the catheter body, the exterior surface of the spring coil and the interior surface of the catheter body defining a predetermined distance therebetween, the predetermined distance being such that the spring coil will transmit torque to the catheter body in response to a change in rotational orientation of the proximal portion of the catheter body when the catheter body is bent;

wherein the coil comprises a wire having a circular cross-section and the ratio of clearance between the exterior surface of the coil and the interior surface of the catheter body to the diameter of the wire, is less than 0.6.

* * * * *